United States Patent
Forton et al.

(10) Patent No.: US 7,901,433 B2
(45) Date of Patent: Mar. 8, 2011

(54) OCCIPITO-CERVICAL STABILIZATION SYSTEM AND METHOD

(75) Inventors: Charles R. Forton, Leander, TX (US); Robert J. Jones, Austin, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 374 days.

(21) Appl. No.: 11/542,786

(22) Filed: Oct. 4, 2006

(65) Prior Publication Data

US 2008/0086124 A1    Apr. 10, 2008

(51) Int. Cl.
*A61B 17/80* (2006.01)
(52) U.S. Cl. .......... 606/250; 606/246; 606/280; 606/279
(58) Field of Classification Search .......... 606/246, 606/247, 250–253, 278–281, 74, 60, 903; 623/17.19; 403/83–84, 87, 110, 362, 386, 403/398

See application file for complete search history.

(56) References Cited

U.S. PATENT DOCUMENTS

| | | |
|---|---|---|
| 4,763,644 A | 8/1988 | Webb |
| 4,805,602 A | 2/1989 | Puno et al. |
| 4,836,193 A | 6/1989 | Ransford |
| 4,841,959 A | 6/1989 | Ransford |
| 4,887,596 A | 12/1989 | Sherman |
| 4,950,269 A | 8/1990 | Gaines |
| 5,129,388 A | 7/1992 | Vignaud et al. |
| 5,360,429 A | 11/1994 | Jeanson et al. |
| 5,498,264 A | 3/1996 | Schlapfer et al. |
| 5,507,745 A | 4/1996 | Logroscino et al. |
| 5,520,689 A | 5/1996 | Schlapfer et al. |
| 5,531,745 A | 7/1996 | Ray |
| 5,542,946 A | 8/1996 | Logroscino et al. |
| 5,545,164 A | 8/1996 | Howland |
| 5,558,674 A | 9/1996 | Heggeness et al. |
| 5,653,708 A | 8/1997 | Howland |
| 5,707,372 A | 1/1998 | Errico et al. |
| 5,713,898 A | 2/1998 | Stucker et al. |
| 5,928,233 A | 7/1999 | Apfelbaum et al. |

(Continued)

FOREIGN PATENT DOCUMENTS

EP    0737449 A1    10/1996

(Continued)

OTHER PUBLICATIONS

U.S. Appl. No. 10/698,049, filed Sep. 2, 2004, Landry.

(Continued)

*Primary Examiner* — Eduardo C Robert
*Assistant Examiner* — Steven J Cotroneo
(74) *Attorney, Agent, or Firm* — Sprinkle IP Law Group

(57) ABSTRACT

A system (10) and associated method are provided for mechanically fixating a region of a skull to a portion of a spine. A plate (20) is provided to contact a region of the skull and be secured thereto. A spinal rod (22) is configured to extend from a location adjacent the plate (20) to a location adjacent at least one vertebra (30). A variable connection (24) is provided to secure the rod (22) to the plate (20). The variable connection (24) has a first mode wherein the relative position of the rod (22) to the plate (20) can be adjusted and a second mode wherein the relative position of the rod (22) to the plate (20) is locked at a particular value selected to maintain a desired curvature of the spine.

26 Claims, 8 Drawing Sheets

U.S. PATENT DOCUMENTS

| | | | |
|---|---|---|---|
| 5,976,135 A | 11/1999 | Sherman et al. | |
| 6,017,343 A | 1/2000 | Rogozinski | |
| 6,077,262 A | 6/2000 | Schlapfer et al. | |
| 6,146,382 A | 11/2000 | Hurlbert | |
| 6,187,005 B1 | 2/2001 | Brace et al. | |
| 6,238,396 B1 | 5/2001 | Lombardo | |
| 6,296,644 B1 | 10/2001 | Saurat et al. | |
| 6,302,883 B1 | 10/2001 | Bono | |
| 6,315,779 B1 | 11/2001 | Morrison | |
| 6,336,927 B2 | 1/2002 | Rogozinski | |
| 6,368,351 B1 | 4/2002 | Glenn | |
| 6,379,358 B1 | 4/2002 | Kuo | |
| 6,432,109 B1 | 8/2002 | Letendart et al. | |
| 6,485,491 B1 | 11/2002 | Farris et al. | |
| 6,524,315 B1 | 2/2003 | Selvitelli et al. | |
| 6,547,790 B2 | 4/2003 | Harkey, III et al. | |
| 6,620,164 B2 | 9/2003 | Ueyama et al. | |
| 6,682,532 B2 | 1/2004 | Johnson | |
| 6,832,999 B2 | 12/2004 | Ueyama et al. | |
| 6,902,565 B2 | 6/2005 | Berger et al. | |
| 6,949,123 B2 | 9/2005 | Reiley | |
| 6,958,065 B2 | 10/2005 | Ueyama et al. | |
| 7,033,377 B2 | 4/2006 | Miller | |
| 7,060,069 B2 | 6/2006 | Kozak et al. | |
| 7,232,441 B2 | 6/2007 | Altarac et al. | |
| 7,250,052 B2 | 7/2007 | Landry et al. | |
| 7,303,563 B2 | 12/2007 | Poyner et al. | |
| 7,491,218 B2 | 2/2009 | Landry et al. | |
| 7,618,443 B2 | 11/2009 | Abdou | |
| 7,621,942 B2 | 11/2009 | Piehl | |
| 2002/0049446 A1 | 4/2002 | Harkey, III | |
| 2002/0120268 A1* | 8/2002 | Berger | 606/61 |
| 2003/0004512 A1 | 1/2003 | Farris et al. | |
| 2003/0036759 A1 | 2/2003 | Musso | |
| 2003/0153913 A1* | 8/2003 | Altarac et al. | 606/246 |
| 2003/0163132 A1 | 8/2003 | Chin | |
| 2003/0176863 A1 | 9/2003 | Ueyama et al. | |
| 2004/0122426 A1 | 6/2004 | Michelson | |
| 2004/0127904 A1 | 7/2004 | Kinieczynski et al. | |
| 2004/0153070 A1 | 8/2004 | Barker et al. | |
| 2004/0172022 A1 | 9/2004 | Landry | |
| 2004/0267259 A1* | 12/2004 | Mazda et al. | 606/246 |
| 2005/0010227 A1 | 1/2005 | Paul | |
| 2005/0080417 A1 | 4/2005 | Alexis et al. | |
| 2005/0119656 A1 | 6/2005 | Ferrante et al. | |
| 2005/0124994 A1 | 6/2005 | Berger et al. | |
| 2005/0216005 A1 | 9/2005 | Howland | |
| 2005/0228382 A1 | 10/2005 | Richelsoph et al. | |
| 2005/0240185 A1 | 10/2005 | Boomer et al. | |
| 2005/0251141 A1 | 11/2005 | Frigg et al. | |
| 2005/0273104 A1 | 12/2005 | Oepen et al. | |
| 2005/0277939 A1 | 12/2005 | Miller | |
| 2005/0283153 A1 | 12/2005 | Poyner et al. | |
| 2005/0288669 A1* | 12/2005 | Abdou | 606/61 |
| 2006/0004359 A1 | 1/2006 | Kramer et al. | |
| 2006/0004360 A1 | 1/2006 | Kramer et al. | |
| 2006/0004363 A1 | 1/2006 | Brockmeyer et al. | |
| 2006/0155283 A1 | 7/2006 | Doherty et al. | |
| 2006/0155284 A1 | 7/2006 | Doherty et al. | |
| 2006/0184170 A1 | 8/2006 | Kapitan et al. | |
| 2006/0217710 A1 | 9/2006 | Abdou | |
| 2006/0217723 A1 | 9/2006 | Suh | |
| 2006/0217724 A1 | 9/2006 | Suh | |
| 2006/0229610 A1 | 10/2006 | Piehl | |
| 2006/0264932 A1 | 11/2006 | Bert | |
| 2007/0016189 A1 | 1/2007 | Lake | |
| 2007/0083201 A1 | 4/2007 | Jones et al. | |
| 2007/0118121 A1* | 5/2007 | Purcell et al. | 606/246 |
| 2007/0123872 A1 | 5/2007 | Brockmeyer et al. | |
| 2007/0299441 A1 | 12/2007 | Hoffman | |
| 2008/0051783 A1 | 2/2008 | Null et al. | |
| 2008/0125781 A1 | 5/2008 | Hoffman | |
| 2008/0147123 A1 | 6/2008 | Schermerhorn | |
| 2008/0177313 A1 | 7/2008 | Lemoine | |
| 2008/0177314 A1 | 7/2008 | Lemoine | |
| 2008/0300635 A1 | 12/2008 | Lieponis | |
| 2009/0270924 A1 | 10/2009 | Wing et al. | |

FOREIGN PATENT DOCUMENTS

| | | |
|---|---|---|
| EP | 1180348 A | 12/2008 |
| FR | 2687561 A1 | 2/1992 |
| FR | 2760629 A1 | 3/1997 |
| WO | WO 9531147 A1 | 11/1995 |
| WO | WO 9723170 A1 | 7/1997 |
| WO | WO 9841160 A1 | 9/1998 |
| WO | WO 2005122922 A2 | 12/2005 |
| WO | WO 2006019370 A1 | 2/2006 |
| WO | WO 2006/096756 A | 9/2006 |
| WO | WO 2006102222 A2 | 9/2006 |
| WO | WO 2007/044716 | 4/2007 |
| WO | WO 2006102222 A3 | 9/2007 |
| WO | WO 2007146482 | 12/2007 |
| WO | WO 2008042633 | 4/2008 |

OTHER PUBLICATIONS

U.S. Appl. No. 10/698,010, filed Jul. 22, 2004, Landry.
U.S. Appl. No. 10/697,793, filed Jul. 15, 2004, Landry.
U.S. Appl. No. 11/234,706, filed Apr. 12, 2007, Jones, et al.
International Search Report for PCT/US2007/079295 issued Apr. 17, 2008.
International Preliminary Report on Patentability, Chapter I, PCT/US2007/085190, mailed Jun. 30, 2009, 8 pages.
International Search Report and Written Opinion, PCT/US2007/085190, mailed Jun. 3, 2008, 13 pages.
Office Action issued in U.S. Appl. No. 11/756,106 mailed Aug. 26, 2009, 7 pages.
Summit SI OCT Spinal Fixation System, undated, 2 pages.
Stryker Spine Products, "Products: Cervical OASYS" Webpage, undated, 1 page.
Blackstone Ascent, Production Information Page, undated, 1 page.
Office Action issued in U.S. Appl. No. 11/085,672 mailed Nov. 17, 2006, Piehl, 9 pages.
Interpore Cross International, "Introducing the Altrius OCT System," Biological & Structural Innovation, Interpore Cross Intl, Irvine, CA, Copyright 2003, 2 pages.
Blackstone Medical Inc., "Ascent Posterior Occipital Cervico-Thoracic System," Cervical and Thoracolumbar Systems, www.blackstonemedical.com., Copyright 2005, 1 page.
Globus Medical, Cervical Webpage, Globus Medical, Copyright 2005, downloaded from http://www.globusmedical.com/products/cervical.php, on Feb. 2, 2006, 1 page.
Globus Medical, Protex CT . . . The new standard in OCT Stabilization systems, www.globusmedical.com, 1-866-456-2871, undated, 1 page.
Depuy Spine, "Mountaineer OCT Spinal System," Copyright 2006, DePuy Spine, Inc., Raynham, MA, Mar. 2005, 6 pages.
Office Action issued in U.S. Appl. No. 11/085,672 mailed May 18, 2007, Piehl, 15 pages.
Office Action issued in U.S. Appl. No. 11/085,672 mailed Nov. 1, 2007, Piehl, 8 pages.
International Search Report and Written Opinion issued in PCT/US2007/066039, mailed Apr. 14, 2008, Zimmer Spine, Inc., 11 pages.
Office Action issued in U.S. Appl. No. 11/085,672 mailed Apr. 29, 2008, Piehl, 9 pages.
Office Action issued in U.S. Appl. No. 11/423,201 mailed Sep. 3, 2008, Hoffman, 15 pages.
Office Action issued in U.S. Appl. No. 11/085,672 mailed Oct. 31, 2008, Piehl, 9 pages.
Office Action issued in U.S. Appl. No. 11/423,201 mailed Dec. 10, 2008, Hoffman, 17 pages.
International Preliminary Report on Patentability and Written Opinion issued in PCT/US2007/066039, mailed Dec. 10, 2008, Zimmer Spine, Inc., 6 pages.
Office Action issued in U.S. Appl. No. 11/423,201 mailed Mar. 5, 2009, 15 pages.
Office Action issued in U.S. Appl. No. 11/085,672 mailed May 7, 2009, Piehl, 12 pages.
Office Action issued in U.S. Appl. No. 11/563,902 mailed May 8, 2009, Hoffman, 9 pages.

International Search Report and Written Opinion issued in PCT/US2006/009996 mailed Jul. 19, 2007, Zimmer Spine, Inc., 10 pages.

International Preliminary Report on Patentability issued in PCT/US2006/009996, mailed Sep. 25, 2007, Zimmer Spine, Inc., 8 pages.

International Preliminary Report on Patentability and Written Opinion issued in PCT/US2007/079295 mailed Apr. 7, 2009, Abbott Laboratories, 7 pages.

Office Action issued in U.S. Appl. No. 11/616,720 mailed May 27, 2009, Lemoine, 8 pages.

Office Action issued in U.S. Appl. No. 11/563,902 mailed Oct. 27, 2009, 10 pgs.

Office Action issued in U.S. Appl. No. 11/423,201 mailed Oct. 29, 2009, 11 pgs.

Office Action issued in U.S. Appl. No. 11/616,720 mailed Dec. 24, 2009, 11 pgs.

Office Action issued in U.S. Appl. No. 11/756,106 mailed Feb. 19, 2010, 6 pgs.

Office Action issued in U.S. Appl. No. 11/616,720 mailed Jun. 10, 2010, 10 pgs.

Office Action issued in U.S. Appl. No. 11/756,106 mailed Sep. 1, 2010, 7 pages.

Examination Report for European Patent Application No. 06738970.0, dated Oct. 21, 2010, European Patent Office, 7 pgs.

Office Action issued in U.S. Appl. No. 11/616,720 mailed Nov. 9, 2010, 11 pages.

Office Action issued in U.S. Appl. No. 12/609,868 mailed Dec. 8, 2010, 16 pgs.

* cited by examiner

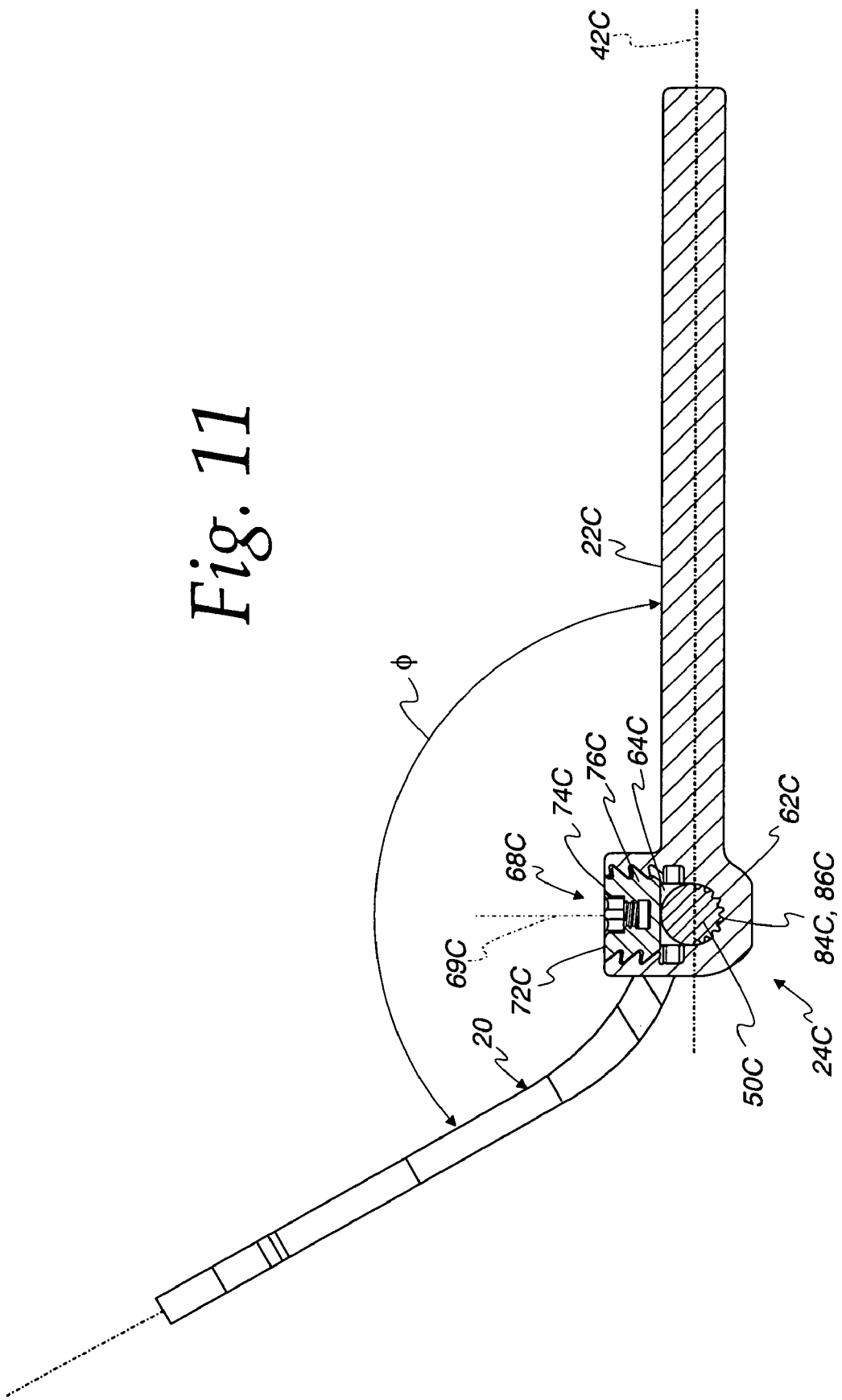

OCCIPITO-CERVICAL STABILIZATION SYSTEM AND METHOD

BACKGROUND OF THE INVENTION

1. Field of the Invention

The present invention generally relates to spinal fixation systems and the like, and in more particular applications, to systems that fixate a portion of the skull to the spine, typically the cervical spine, for correction, fixation, and/or stabilization of a human spine.

2. Description of the Related Art

Spinal fixation, such as lumbar sacral fusion and the correction of spinal deformities such as scoliotic curves, is a well known and frequently used medical procedure. Pedicle, lateral, and oblique mounting devices may be used to secure corrective spinal instrumentation to a portion of the spine that has been selected to be fused by arthrodesis.

A spinal fixation system typically includes corrective spinal instrumentation that is attached to selected vertebra of the spine by screws, hooks, and clamps. The corrective spinal instrumentation includes spinal rods or plates that are generally parallel to the patient's back. The corrective spinal instrumentation may also include transverse connecting rods that extend between neighboring spinal rods. Spinal fixation systems are used to correct problems in the lumbar and thoracic portions of the spine, and are often installed posterior to the spine on opposite sides of the spinous process and adjacent to the transverse process.

Various types of screws, hooks, and clamps have been used for attaching corrective spinal instrumentation to selected portions of a patient's spine. Examples of pedicle screws and other types of attachments are illustrated in U.S. Pat. Nos. 4,763,644; 4,805,602; 4,887,596; 4,950,269; and 5,129,388. Each of these patents is incorporated by reference as if fully set forth herein.

Fixation of the skull to the cervical spine may be used to treat trauma to the neck, degenerative diseases such as rheumatoid arthritis, and pain that is otherwise unresponsive to treatment. Current implantable devices designed to immobilize the skull with respect to the upper cervical spine have to be individually tailored. Often, such devices are assemblies of several components not designed specifically for fusing the cervical spine to the skull. However, devices specifically designed for fusing the cervical spine to the skull are currently being introduced. U.S. Pat. No. 6,146,382 issued to John Hurlbert on Nov. 14, 2000, shows one such device and is incorporated herein by reference as if full set forth herein.

SUMMARY OF THE INVENTION

In accordance with one feature of the invention, a system is provided for mechanically fixating a region of a skull to a portion of a spine. The system includes a plate configured to contact the region of the skull and be secured thereto, a spinal rod configured to extend from a location adjacent to the plate for connection thereto to a location adjacent at least one vertebra for connection thereto, the rod forming an angle $\phi$ with respect to the plate about a transverse axis, and a variable connection configured to secure the rod to the plate. The variable connection has a first mode connecting the rod and the plate wherein the angle $\phi$ can be freely varied without requiring deformation of the rod and the plate and a second mode connecting the rod and the plate wherein the rod and the plate are locked at a particular value of the angle $\phi$ selected to maintain a desired curvature of the spine.

As one feature, the connection is configured to also allow the rod to be adjusted laterally with respect to the plate in the first mode without requiring deformation of the rod and the plate, and to be locked at a lateral position relative to the plate in the second mode.

According to one feature, the connection is configured to also allow the rod to be adjusted longitudinally with respect to the plate in the first mode without requiring deformation of the rod and the plate, and to be locked at a longitudinal position relative to the plate in the second mode.

In one feature, the connection is configured to allow a second angle formed between the rod and the plate to be adjusted in the first mode without requiring deformation of the rod and the plate, and for the rod and the plate to be locked at a particular value of the second angle in the second mode.

In accordance with one feature, the variable connection includes a lateral arm integral with the plate and extending laterally along the transverse axis relative to the spine, and a connector including a body having a transverse opening configured to receive the arm and a longitudinal opening configured to receive a proximate portion of the rod adjacent the plate. The transverse opening is configured to pivot freely about the transverse axis in the first mode and to lock to the arm in the second mode.

As one feature, the lateral arm and the transverse opening are configured to also allow the connector to be adjusted laterally with respect to the plate in the first mode without requiring deformation of the rod and the plate, and to be locked at a lateral position relative to the plate in the second mode.

In one feature, the longitudinal opening is configured to also allow the rod to be adjusted longitudinally with respect to the plate in the first mode without requiring deformation of the rod and the plate, and to be locked at a longitudinal position relative to the plate in the second mode.

According to one feature, the lateral arm and the transverse opening are configured to allow a second angle formed between the rod and the plate to be adjusted in the first mode without requiring deformation of the rod and the plate, and for the rod and the plate to be locked at a particular value of the second angle in the second mode.

In accordance with one feature, the body has a lock opening connecting the transverse and longitudinal openings and extending normal to the transverse and longitudinal openings. The connector further includes a clamp plug configured to be received in the lock opening at a location between the transverse and longitudinal openings, and a lock configured to engage the lock opening and clamp the clamp plug, the lateral arm, and the rod in the second mode.

As one feature, the lateral arm has a first set of spline teeth and the plug has a second set of spline teeth, the first and second sets of spline teeth being disengaged in the first mode and engaged in the second mode.

In one feature, the lock has external threads and the locking opening has internal threads that mate with the lock in both the first and second modes.

According to one feature, the body has first and second lock openings, with the first lock opening extending into the transverse opening, and second lock opening extending into the longitudinal opening. The connector further includes first and second locks. The first lock is configured to engage the first lock opening and clamp the lateral arm to the body, and the second lock is configured to engage the second lock opening and clamp the rod to the body.

As a further feature, each of the locks have external threads and each of the locking openings has internal threads that mate with the corresponding lock in both the first and second modes.

In accordance with one feature, the system further includes a second spinal rod and a second variable connection. The second spinal rod is configured to extend from a location adjacent to the plate for connection thereto to a location adjacent at least one vertebra for connection thereto. The first and second rods are positioned on laterally opposite sides of the plate from each other. The second variable connection is configured to secure the second rod to the plate, with the second connection having a first mode connecting the second rod and the plate wherein an angle formed between the second rod and the plate can be freely varied without requiring deformation of the second rod and the plate, and a second mode connecting the second rod and the plate wherein the second rod and the plate are locked at a particular value of the angle selected to maintain a desired curvature of the spine.

In accordance with one feature of the invention, a system is provided for mechanically fixating a region of a skull to a portion of a spine. The system includes a plate configured to contact the region of the skull and be secured thereto, a spinal rod configured to extend from a location adjacent to the plate for connection thereto to a location adjacent at least one vertebra for connection thereto, and a variable connection configured to secure the rod to the plate. The connection has first and second modes connecting the rod and the plate. In the first mode, a relative position of the rod and the plate is adjustable with respect to at least four degrees of freedom of motion without requiring deformation of the rod and the plate. In the second mode, the rod and the plate are locked in a particular relative position with respect to the at least four degrees of freedom of motion to maintain a desired curvature of the spine.

As one feature, the variable connection is configured to allow adjustment of the relative position for the rod and the plate with respect to a fifth degree of freedom of motion in the first mode without requiring deformation of the rod and the plate.

According to one feature, one of the degrees of freedom of motion is a rotation about a laterally extending axis.

In one feature, another one of the degrees of freedom of motion is a rotation about an axis that is perpendicular to both a laterally extending axis and a longitudinally extending axis.

As one feature, another one of the degrees of freedom of motion is a translation along the laterally extending axis.

In accordance with one feature, another one of the degrees of freedom of motion is a translation along a longitudinally extending axis.

According to one feature, another one of the degrees of freedom of motion is a rotation about a longitudinally extending axis.

As one feature, the variable connection includes a lateral arm integral with the plate and extending laterally relative to the spine, and a connector including a body having a transverse opening configured to receive the arm and a longitudinal opening configured to receive a proximate portion of the rod adjacent the plate. The transverse opening is configured to pivot about the arm and slide along the arm in the first mode and to lock to the arm in the second mode. The longitudinal opening is configured to allow the rod to rotate about a longitudinal axis defined by the rod and to slide along the longitudinal axis in the first mode and to lock to the rod in the second mode.

In one feature, the transverse opening is configured to pivot relative to the arm about an axis perpendicular to both the longitudinal axis and a laterally extending axis defined by the arm in the first mode.

According to one feature, the system further includes a second spinal rod and a second variable connection. The second rod is configured to extend from a location adjacent to the plate for connection thereto to a location adjacent at least one vertebra for connection thereto, with the first and second rods positioned on laterally opposite sides of the plate from each other. The second variable connection is configured to secure the second rod to the plate, the second connection having first and second modes connecting the second rod and the plate. In the first mode, a relative position of the second rod and the plate is adjustable with respect to at least four degrees of freedom of motion without requiring deformation of the second rod and the plate. In the second mode, the second rod and the plate are locked in a particular relative position with respect to the at least four degrees of freedom of motion to maintain a desired curvature of the spine.

In accordance with one feature of the invention, a method is provided for coupling a plate to a rod in a system where the plate is to be secured to a region of a skull and the rod is to be secured to at least one vertebra of a spine. The method includes the steps of:

connecting the rod to the plate so that there is a relative angle $\phi$ formed between the rod and a plane defined by the plate;

adjusting the relative angle $\phi$ to a particular value of the angle $\phi$ selected to maintain a desired curvature of the spine without requiring deformation of the rod or the plate; and the rod and the plate to prevent movement from the particular value of the angle $\phi$.

As one feature, the method further includes the step of adjusting a lateral position of the rod relative to the plate without requiring deformation of the rod or the plate.

In one feature, the method further includes the step of adjusting a longitudinal position of the rod relative to the plate without requiring deformation of the rod or the plate.

According to one feature, the method further includes the step of adjusting an angular position of the rod relative to the plate about an axis that is perpendicular to both a laterally extending axis and a longitudinally extending axis without requiring deformation of the rod or the plate.

As one feature, the method further includes the step of adjusting an angular position of the rod relative to the plate about a longitudinal axis defined by the rod without requiring deformation of the rod or the plate.

According to one feature, the method further includes at least three of the following steps:

adjusting a lateral position of the rod relative to the plate without requiring deformation of the rod or the plate;

adjusting a longitudinal position of the rod relative to the plate without requiring deformation of the rod or the plate;

adjusting an angular position of the rod relative to the plate about an axis that is perpendicular to both a laterally extending axis and a longitudinally extending axis without requiring deformation of the rod or the plate; and an angular position of the rod relative to the plate about a longitudinal axis defined by the rod without requiring deformation of the rod or the plate.

In accordance with one feature of the invention, a method is provided for coupling a plate to a rod in a system where the plate is to be secured to a region of a skull and the rod is to be secured to at least one vertebra of a spine. The method includes the steps of:

connecting the rod to the plate;

adjusting a relative position of the rod and the plate with respect to at least four degrees of freedom of motion; and locking the rod and the plate at a particular relative position with respect to the at least four degrees of freedom of motion to maintain a desired curvature of the spine.

As one feature, one of the degrees of freedom of motion is a rotation about a laterally extending axis.

In one feature, another one of the degrees of freedom of motion is a rotation about an axis that is perpendicular to both a laterally extending axis and a longitudinally extending axis.

According to one feature, another one of the degrees of freedom of motion is a translation along the laterally extending axis.

As one feature, another one of the degrees of freedom of motion is a translation along a longitudinally extending axis.

In accordance with one feature, another one of the degrees of freedom of motion is a rotation about a longitudinally extending axis.

In one feature, the adjusting step is performed after the connecting step and before the locking step.

Other features, objects, and advantages of the invention will become apparent after a detailed review of the entire specification, including the appended claims and drawings.

BRIEF DESCRIPTION OF THE DRAWINGS

FIG. 11 is a side or lateral section view taken from line 11-11 in FIG. 10.

DETAILED DESCRIPTION OF THE PREFERRED EMBODIMENT

Figure 2:
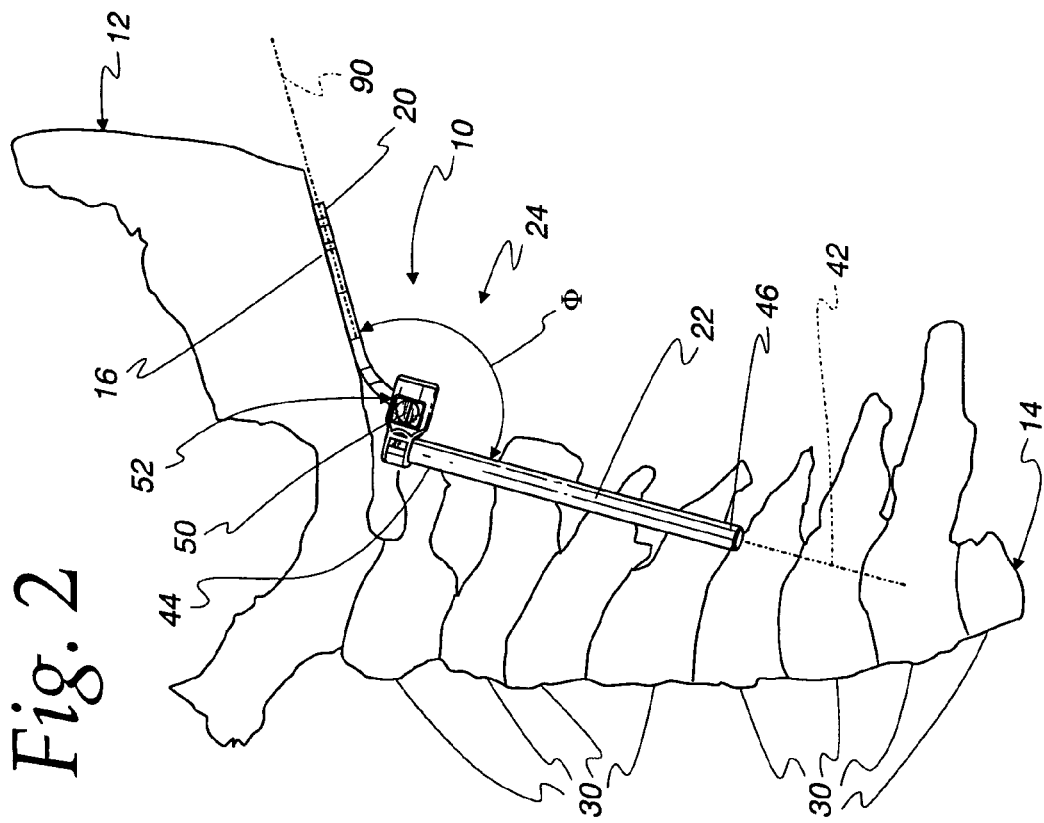
FIGS. 1 and 2 depict an occipito-cervical spinal fixation system embodying the present invention in use, with FIG. 1 being a view looking upward along a portion of a spinal column toward an occiput of a skull, and FIG. 2 being a lateral view.
Figure 1:
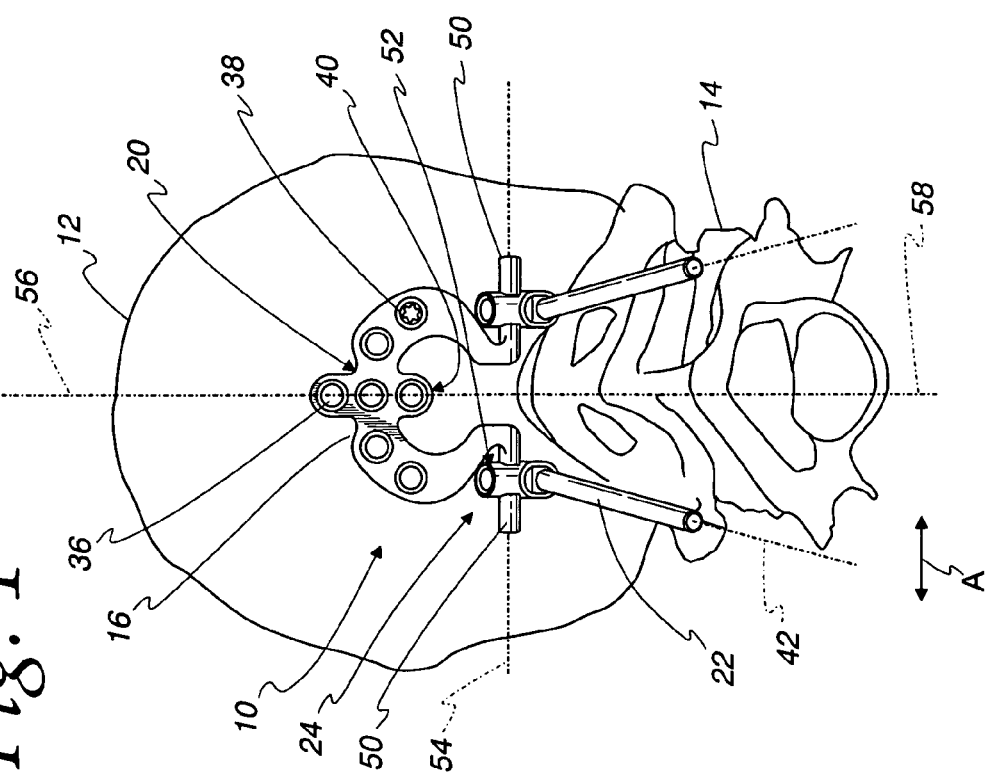
Figure 3:
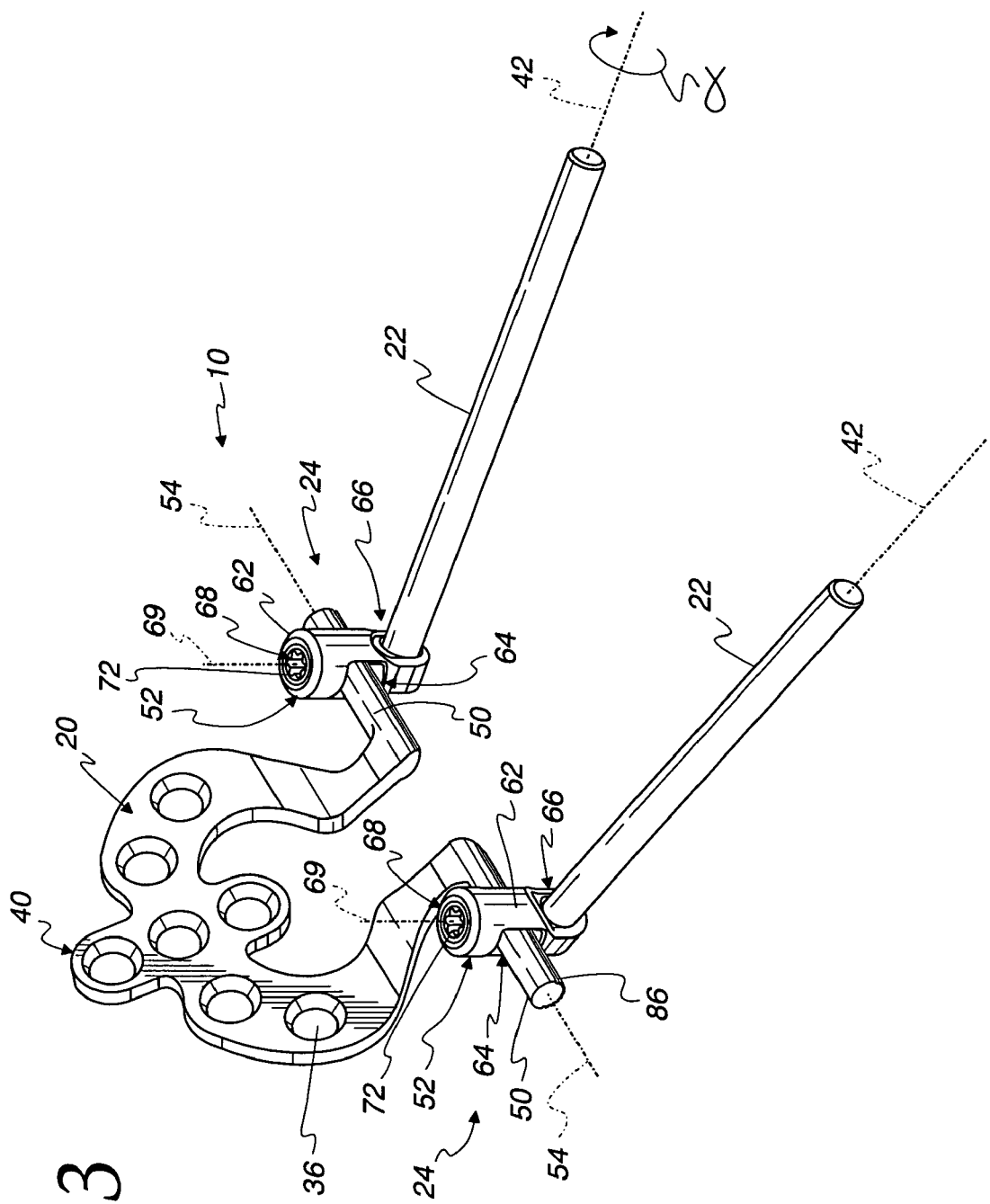
FIG. 3 is a perspective view showing selected components of the fixation system of FIGS. 1 and 2.
Figure 4:
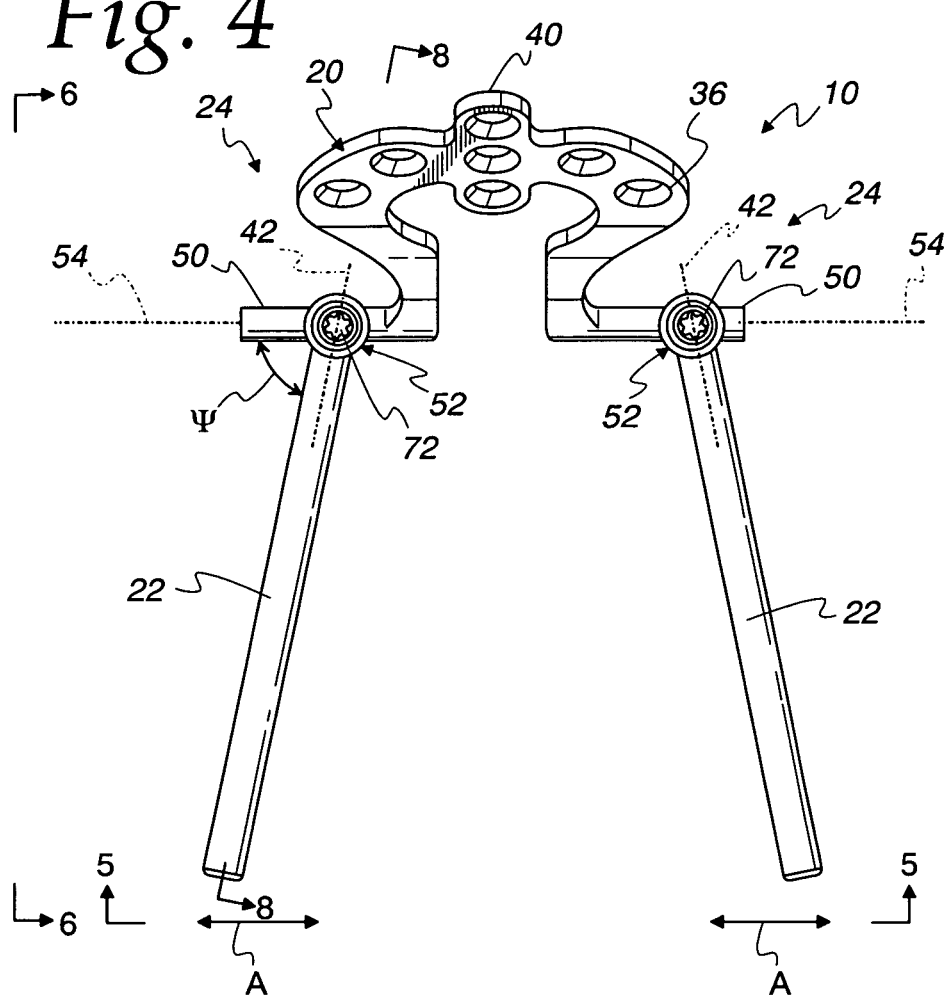
FIG. 4 is a plan or posterior view of the fixation system of FIG. 3.
Figure 5:
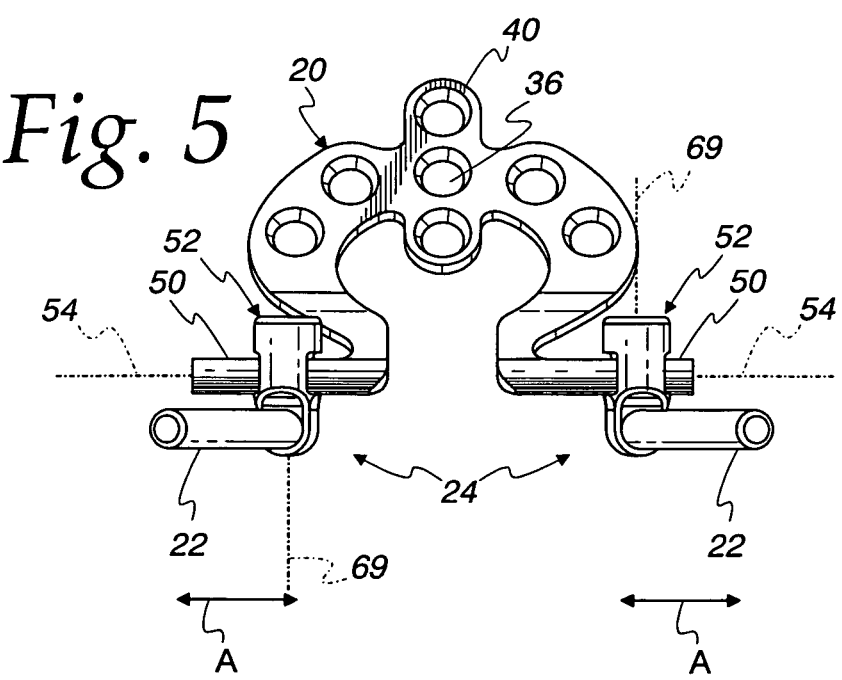
FIG. 5 is a bottom view taken from line 5-5 in FIG. 4.
Figure 6:
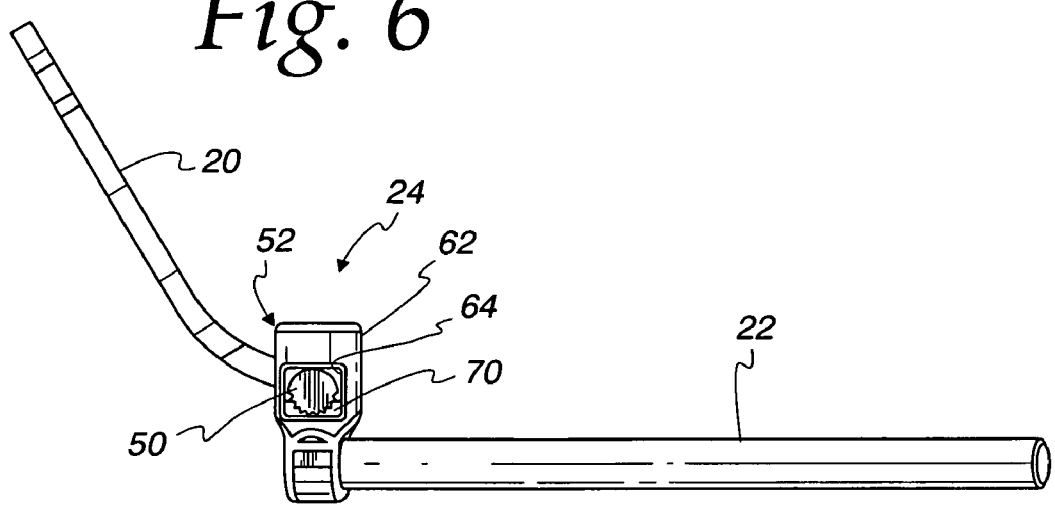
FIG. 6 is a side or lateral view taken from 6-6 in FIG. 4.

With reference to FIGS. 1 and 2, an occipito-cervical spinal fixation system 10 is shown for mechanically fixating a region of a skull 12 to a portion of a spinal column 14. The system 10 includes a plate 20, at least one spinal rod 22, (but more typically two of the spinal rods 22) and a variable connection, shown generally by arrow 24, for each spinal rod 22.

The plate 20 is configured to contact the occiput or occipital bone 16 of the skull and be secured thereto. The spinal rod 22 is configured to extend from a location adjacent the plate 20 for connection thereto to a location adjacent at least one of the vertebra 30 of the spine 14 for connection thereto. The variable connection 24 is configured to connect the rod 22 to the plate 20 in first and second modes, with the first mode connecting the plate 20 and rod 22 while allowing the relative position of the rod 22 to the plate 20 to be adjusted without requiring deformation of the rod 22 and the plate 20, and the second mode locking the plate 20 and the rod 22 at a particular relative position to maintain a desired positioning of the skull 20 and spine 14. In this regard the components of the fixation system are preferably configured to substantially immobilize the skull 12 with respect to the spinal column 14 during use with the connection 24 in the second mode. The components of the fixation system 10 are preferably made from a suitable biocompatible material, such as titanium or stainless steel.

The plate 20 preferably includes a plurality of openings 36 formed therein for receiving connecting members 38. During use, connecting members 38 may be inserted into holes formed in the skull 12 to secure the plate 20 to the occiput 16 such that movement of the skull 12 with respect to a portion of the spine is inhibited. In this regard, connecting members 38 preferably are a suitable bone screw, many of which are known.

While any shape may be used for the plate 20, it is preferred that the plate 20 have a shape that generally conforms to the occiput 16, with the illustrated horseshoe shape being highly preferred because it offers multiple options for placement of the openings 36 and the associated connecting members 38 and is compatible with the use of two laterally positioned rods 22, which is typical of most spinal fixation systems. It is also preferred that the plate 20 include a central portion 40 that extends longitudinally to provide multiple possible locations for the openings 36 and the associated connecting members 38 central to the occiput 16.

The rod 22 supports and preferably immobilizes one or more levels of the spine 14 and can be of any suitable construction, many of which are known. Typically, as shown in the illustrated embodiment, the rod 22 will be in the form of a straight, cylindrically shaped metallic rod extending along a longitudinal axis 42 and formed of a suitable biocompatible material that can be deformed along its length as required to conform to the patient morphology. However, it should be understood that pre-bent or pre-deformed rods and/or noncylindrical rods can also be used in the system 10. The rod 22 has a proximate end portion 44 that is adjacent the plate 20 for connection thereto, and a length extending to a distal end portion 46 adjacent at least one of the vertebra 30. Typically, at least the distal end 46 of the rod 22, and potentially other portions of its length, will be affixed to at least one of the vertebra 30 using a suitable anchoring system, many of which are known and which will typically include a bone screw or bolt and some sort of rod connector that is either integral with the bone screw or otherwise connectable to the bone screw.

The variable connection 24 includes a lateral arm 50 and a connector 52. Preferably, the lateral arm 50 is formed integral with the plate 20 and extends laterally along a transverse axis 54 relative to the spine. Preferably, in use, the arm 50 and axis 54 are normal to the mid-sagittal plane, shown schematically by dashed line 56 in FIG. 1 and to the longitudinal axis, shown schematically at 58 in FIG. 1, of the spine 14 lying in the mid-sagittal plane. The connector 52 connects the arm 50 and the rod 22 and allows for adjustment of the relative position between the arm 50 and the rod 22 while the rod 22 and the arm 50 are connected in the first mode.

Figure 7:
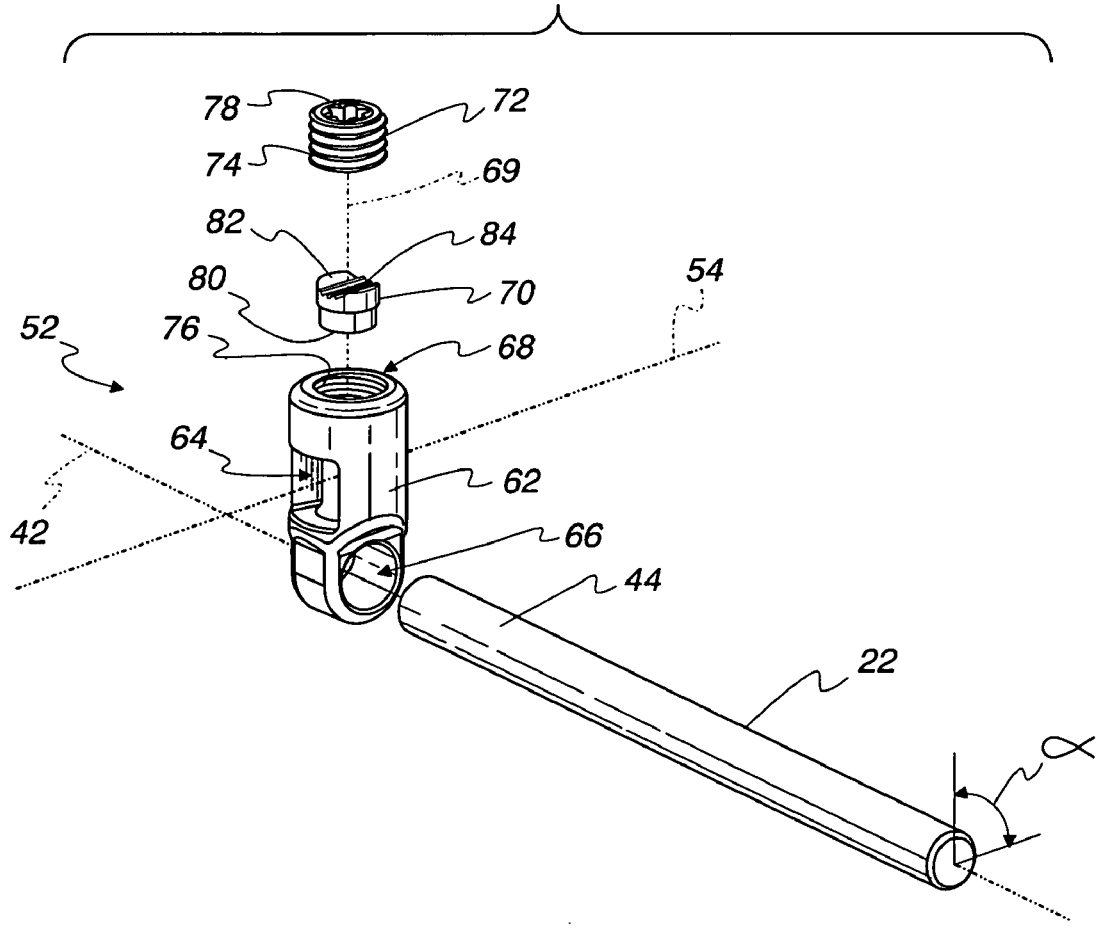
FIG. 7 an exploded, perspective view showing selected components of the fixation system of FIGS. 1-6.

As best seen in FIG. 7, the connector 52 includes a body 62 having a transverse opening 64 configured to receive the arm 50, a longitudinal opening 66 configured to receive the proximate end portion 44 of the rod 22, and a lock opening 68, preferably extending along an axis 69 that is aligned with and perpendicular to both the transverse and longitudinal openings 64,66 to connect the transverse and longitudinal openings 64,66. Preferably, the transverse opening 64 is oversized at each end with respect to the outer surface of the lateral arm 50 in order to allow pivoting of the body 62 on the arm 50 about the axis 69 in the first mode. The connector 52 further includes a clamp plug 70 and a lock 72 that are received in the lock opening 68 and preferably are configured to operate in the opening 68 to allow free rotational and translational movement of the arm 50 and the rod 22 in the respective openings 64 and 66 in the first mode, and to clamp the arm 50 and the rod 22 against rotational and translational movement in the respective openings 64 and 66 in the second mode.

Figure 8:
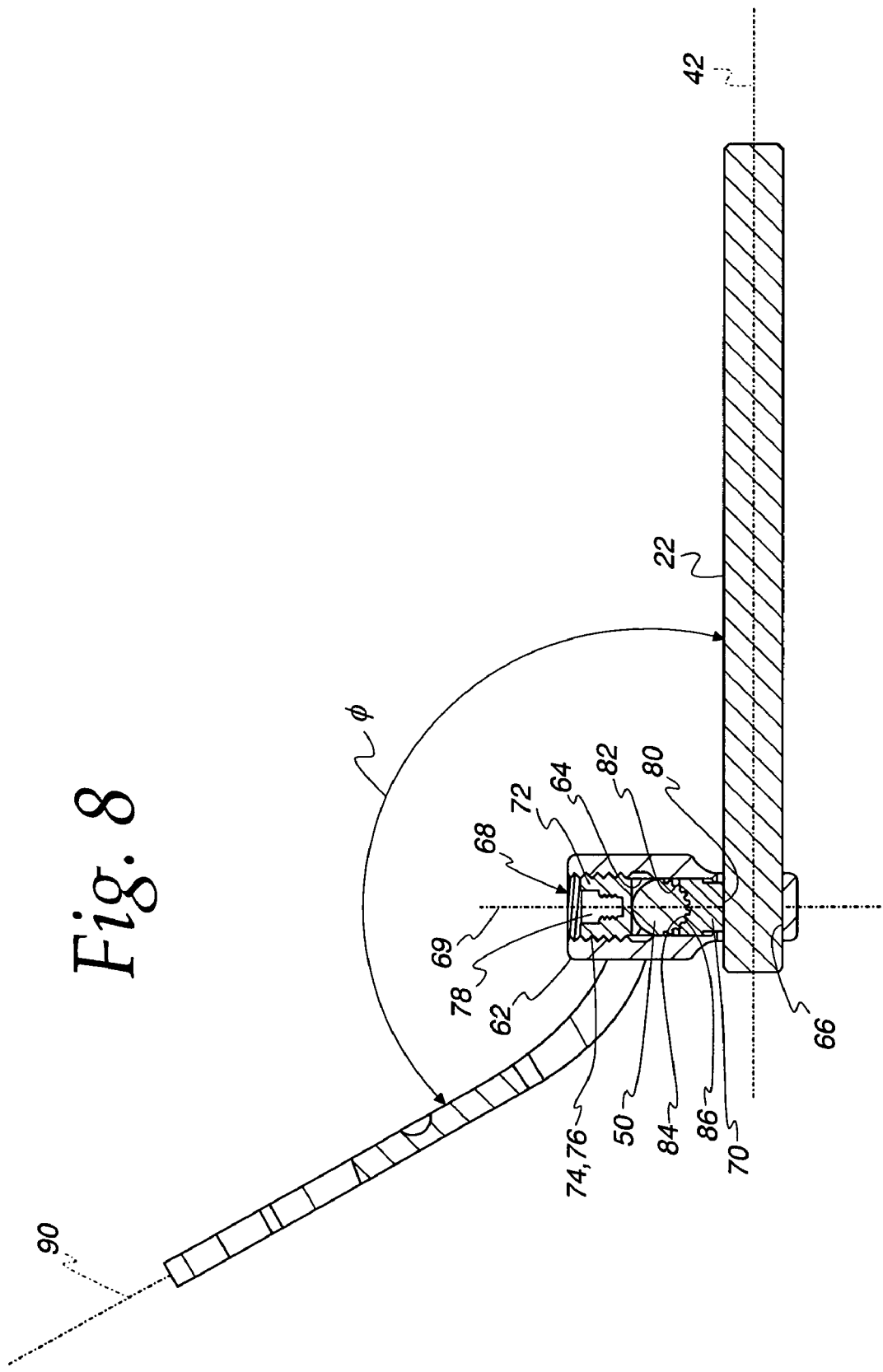
FIG. 8 is a section view taken from line 8-8 in FIG. 4.
Figure 9:
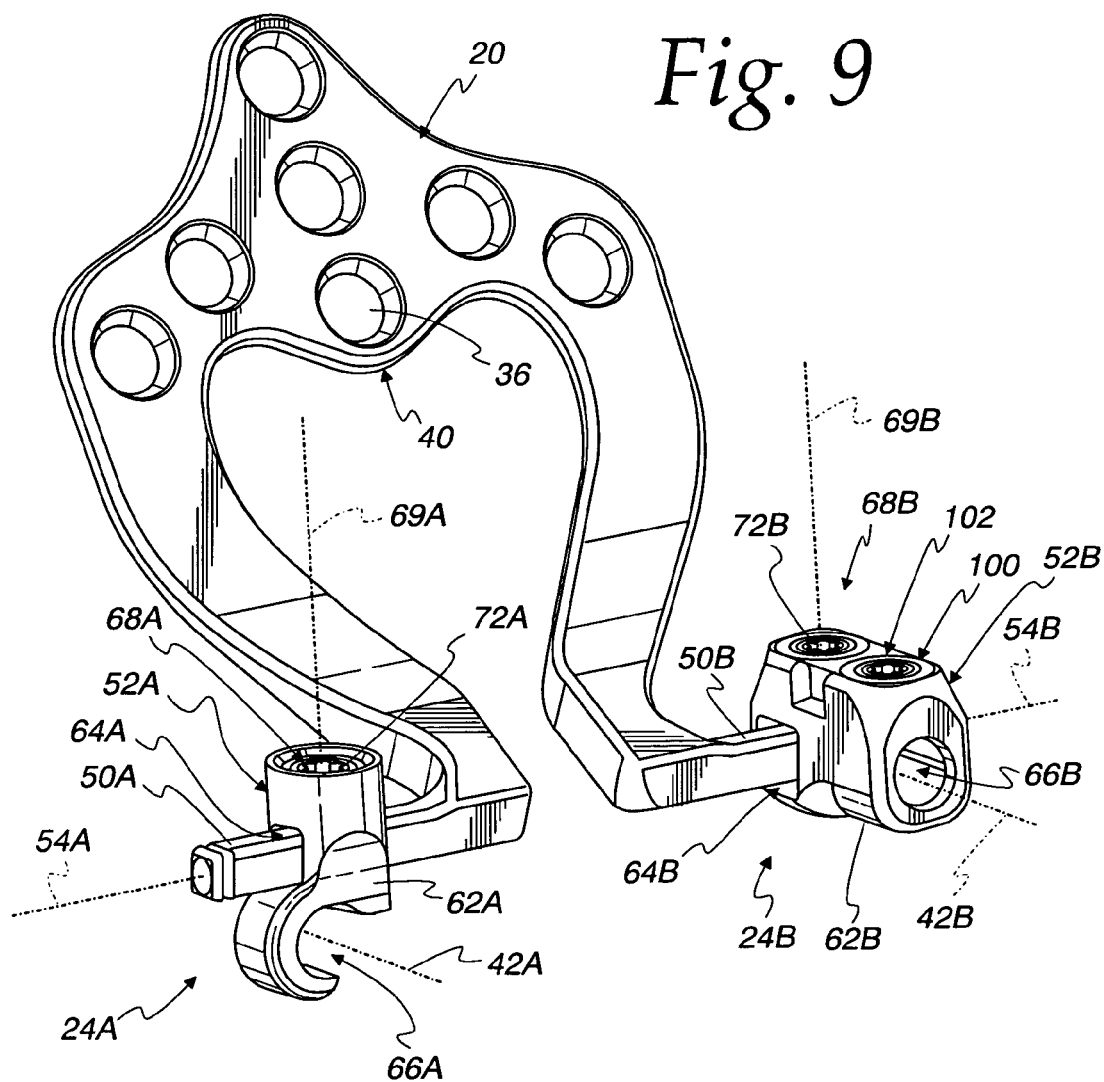
FIG. 9 is a perspective view showing alternate embodiments for selected components of the fixation system.

As best seen in FIG. 8, the clamp plug 70 is configured to be received in the lock opening 68 at a location between the transverse and longitudinal openings 64, 66, and the lock 72 is configured to engage the lock opening 68 and clamp the clamp plug 70, the lateral arm 50, and the rod 22 in the second mode. As best seen in FIG. 7, the lock 72 is preferably a threaded fastener, such as set screw, that has external threads 74 which engage internal threads 76 formed in an upper portion of the lock opening 68, and a drive feature 78 that can be engaged by a tool to rotate the lock 72 relative to the body 62. The clamp plug 70 preferably has a surface 80 that abuts the outer surface of the rod 22 in the second mode, and further has a U-shaped surface 82 for receiving the lateral arm 50, with the surface 82 being shaped to conform to the outer periphery of the lateral arm 50. As best seen in FIGS. 7-8, in a preferred embodiment, the surface 82 includes a plurality of spline teeth 84 that mate with corresponding spline teeth 86 that are preferably provided on the lateral arm 50. In this regard, the spline teeth 86 can be provided over a limited extent of the circumferential periphery of the arm 50, or can be provided around the entire circumferential periphery of the arm. Preferably, the spline teeth 86 extend parallel to the axis 54 over the length of the arm 50. It will be appreciated that in the second mode, as shown in FIG. 9, the mating engagement of the spline teeth 84,86 serves to react torsional loading about the axis 54 and maintain the rod 22 in its desired position relative to the plate 20 when the system 10 is in use.

In the first mode, the lateral arm 50 is received in the transverse opening 64 and the proximate end of the rod 22 is received in the longitudinal opening 66, with the clamp plug 70 received in the lock opening 68 at a position between the arm 50 and the rod 22. The lock 72 is engaged in the lock opening 68 at a position wherein the spline teeth 84,86 are disengaged to allow the body 62 to freely rotate and translate about and along the arm 50 and to freely pivot about the axis 69, and wherein the rod 22 can freely rotate and translate about and along the longitudinal axis 42 in the longitudinal opening 66.

It will be appreciated from the foregoing that the variable connection 24 allows the relative position of the rod 22 to the plate 20 to be adjusted with respect to five degrees of freedom of motion in the first mode if required to fit patient morphology during a surgical procedure. One degree of freedom of motion is the rotation or pivoting of the body 62 about the arm 50 and transverse axis 54, which allows adjustment of an angle φ that is formed between the rod 22 and a plane 90 defined by the plate 20, as best seen in FIG. 2. In anatomical terms, the angle φ can be said to lie in a sagittal plane, and is critical in positioning the skull 12 relative to the spine 14 and defining the curvature of the spine 14. Depending on patient morphology, the angle φ will most often be between 100° and 150°, but can be any angle required to provide the desired or natural curvature of the spine 14. Another degree of freedom of motion is the translation of the body 62 along the lateral arm 50 and transverse axis 54, shown by arrows A in the Figs., which allows for the lateral position of the rod 22 to be adjusted relative to the spine 14 to fit patient morphology. Pivoting of the body 62 about the axis 69 provides another degree of freedom of motion and allows for adjustment of an angle Ψ formed between the rod 22 and the arm 50 and axis 54. Another degree of freedom is the translation of the rod 22 in the longitudinal opening 66 along the longitudinal axis 42 relative to the body 62, which allow for adjustment of the longitudinal position of the rod 22 relative to the plate 20 and the spine 14. Finally, rotation of the rod 22 about the axis 42 provides yet another degree of freedom of motion and allows for adjustment of an angle α that can be critical if the rod 22 had been deformed along its length to better conform to patient morphology or if the rod 22 requires a particular angle α so as to more easily mate with a corresponding anchoring system for the rod 22 to the spine 14. It should be appreciated that with the system 10 in the first mode, all of the foregoing adjustments can be made during a surgical procedure with the system 10 positioned in its desired location relative to the skull 12 and spine 14, thereby allowing a surgeon to more easily adjust the system 10 to the patient morphology.

After the desired relative position of the rod 22 to the plate 20 has been selected by the surgeon in order to provide the desired positioning of the spine and skull (i.e., after the system 10 has been fitted to the patient), the variable connection 24 is placed in the second mode by further engaging the lock 72 in the lock opening 68 so as to clamp the lateral arm 50 against the clamp plug 70 (with the spline teeth 84, 86 engaged), the clamping plug 70 against the rod 22, and the rod 22 against the inner surface of the longitudinal opening 66, thereby locking the rod 22 and the plate 20 in the desired relative position, as best seen in FIG. 8.

While all of the above adjustments can be important, it is believed that the ability to adjust the angle φ in the first mode and then to lock the angle φ in the second mode so as to resist the torsion placed on the system 10 in use provides a unique advantage over current known fixation systems. Furthermore, it is also believed that the ability to adjust the relative position of the rod 22 to the plate 20 with respect to at least four degrees of freedom in the first mode provides another unique advantage over current known fixation systems.

The system 10 according to the invention may be used in minimally invasive surgery (MIS) procedures or in non-MIS procedures, as desired, and as persons of ordinary skill in the art who have the benefit of the description of the invention understand. MIS procedures seek to reduce cutting, bleeding, and tissue damage or disturbance associated with implanting a spinal implant in a patient's body. Exemplary procedures may use a percutaneous technique for implanting longitudinal rods and coupling elements. Examples of MIS procedures and related apparatus are provided in U.S. patent application Ser. No. 10/698,049, filed Oct. 30, 2003, U.S. patent application Ser. No. 10/698,010, filed Oct. 30, 2003, and U.S. patent application Ser. No. 10/697,793, filed Oct. 30, 2003, incorporated herein by reference.

The system 10 according to the invention is suitable for use with MIS procedures because the locks 72 are tightened or fastened from above. In such an MIS procedure, the surgeon may percutaneously position and place the system 10 using the same technique and through the same wound exposure as with other spinal implants, then tighten or fasten the locks 72. Because locks 72 can be accessible through the wound, one may couple the components 20, 22 and 24 together by tightening the locks 72, as described above in detail, without using additional incisions or wounds.

It should be appreciated that there are many possible variations for the components of the system 10. For example, with reference to FIG. 9, two alternate embodiments are shown for the variable connection 24. Specifically, the variable connection 24A shown on the left in FIG. 9 is similar to the variable connection 24 shown in FIGS. 3-8, but differs in that its lateral arm 50A is provided with a square spline, as opposed to having a plurality of spline teeth. Furthermore, the longitudinal opening 66A of the connector 52A is offset laterally with respect to the axis 69A of the lock opening 68A, and is a so-called "open" type construction wherein the structure of the body 62A has a hook-shaped configuration that only partially encircles the longitudinal opening 66A. The details of the connector 52A are more thoroughly described in co-pending U.S. patent application Ser. No. 11/234,706, filed on Nov. 23, 2005 and naming Robert J. Jones and Charles R. Forton as inventors (the contents of this application are incorporated fully herein by reference). The variable connection 24B shown on the right-hand side of FIG. 9 also utilizes a lateral arm 50B having a square spline, and has a connector 52B that differs significantly from the connectors 52 and 52A. More specifically, the longitudinal opening 66B in the connector 52B extends along an axis 42B that intersects the transverse axis 54B, rather than being offset as in the connectors 52 and 52A. Furthermore, the connector 52B has no clamp plug 70, but rather utilizes a second locking opening 100 and a second lock 102 that engages in the lock opening 100 to clamp the rod 22 in the longitudinal opening 66B in the second mode. Also, the lock 72B engages in the lock opening 64B to clamp the arm 52B directly in the lateral opening 64B. While the variable connector 24B requires manipulation of the additional lock 102 so as to place the connection 24B in the second mode, it can provide a more compact construction in the anterior-posterior direction in comparison to the variable connections 24 and 24B because of the alignment of the axis 42B with the axis 54B. It will be appreciated that the square splines for the arms 50A and 50B shown in FIG. 9 will significantly limit the adjustment with respect to the angle ϕ. However, it should be appreciated that the lateral arms 52 of FIGS. 3-6 utilizing the multiple spline teeth could be utilized with the connectors 52A and 52B. Furthermore, it should be appreciated that other types of splines and anti-rotation type connections can be utilized with the variable connections 24,24A,24B.

As another example, although the connectors 52 are shown so that the longitudinal opening 66 is positioned on the anterior side of the lateral arm 50, it is possible to modify the connector 52 so that the longitudinal opening 66 is located on the posterior side of the lateral arm 50. In this regard, it would still be desirable for the lock 72 to be accessible from the posterior side.

Figure 10:
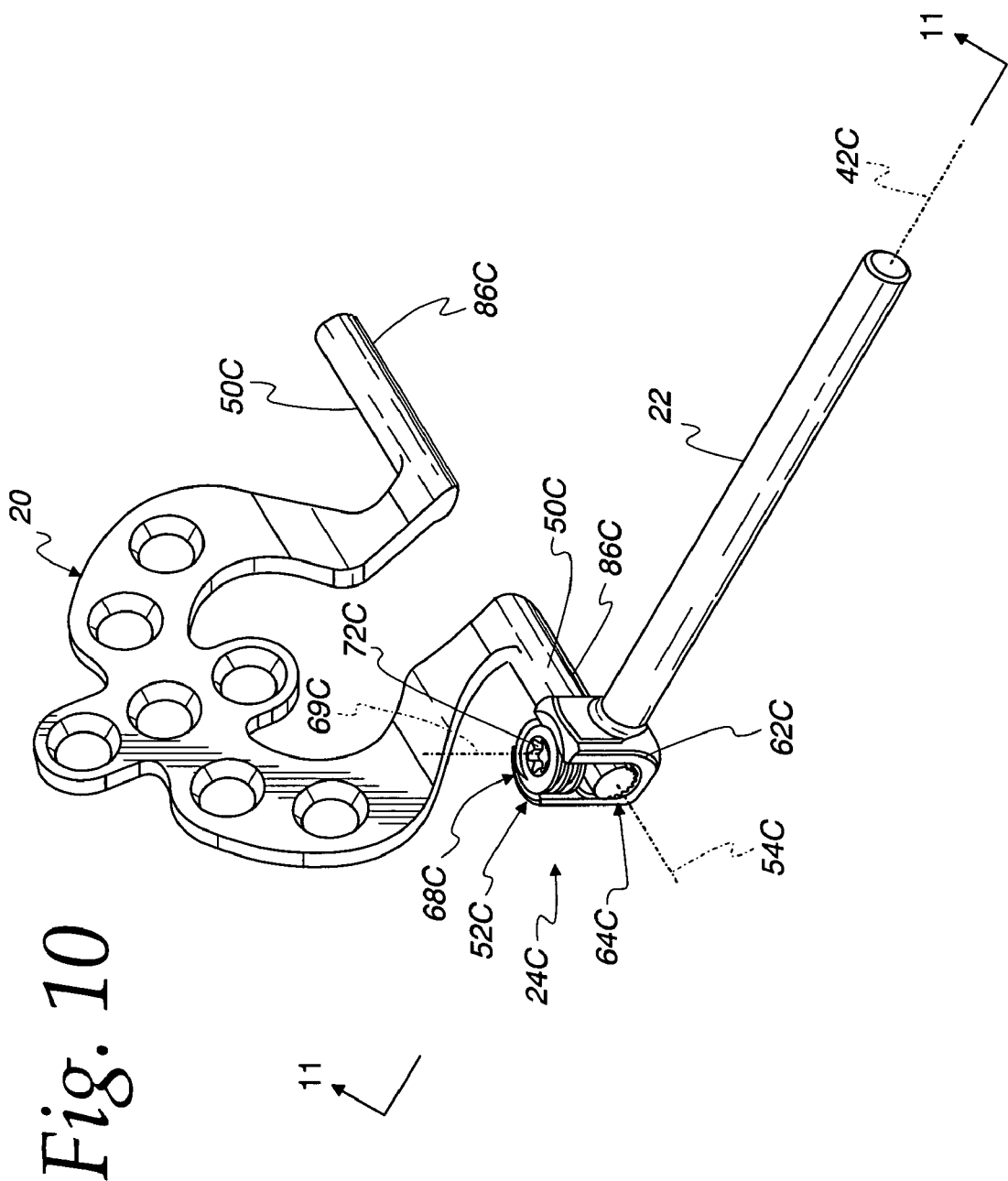
FIG. 10 is a perspective view showing another alternate embodiment for selected components of the fixation system.

As yet another example, FIGS. 10 and 11 show yet another alternate embodiment for the system 10 that differs from the other embodiments in that the body 62C of the variable connection 24C has been integrated with the rod 22C. In this regard, because the rod 22C and body 62C are an integrated component, there is no longer a need for the body 62C to have a longitudinal opening 66, nor is there a need for a clamp plug 70 or any other component to connect the rod 22C to the body 62C. In view of this, the body 62C has only the transverse opening 64C, the lock opening 68C, and the lock 72C, with the spline teeth 84C being formed on the body 62C within the transverse opening 64C. While this simplifies the construction of the variable connection 24 in comparison to the previously discussed variable connections 24, 24A and 24B, it also eliminates the ability to adjust the longitudinal position of the rod 22C relative to the plate 20 and spine 14, as well as the rotational position of the rod 22C about the longitudinal axis 42C.

Persons skilled in the art may make various changes in the shape, size, number, and/or arrangement of parts without departing from the scope of the invention as described herein. In this regard, it should also be appreciated that the various relative dimensions of each of the components 20, 22 and 24 are shown in the figures for purposes of illustration only and may be changed as required to render the system 10 suitable for its intended purpose. For example, the length of the lateral arms 52 may desirably be shorter or longer depending upon how much adjustment of the rods 22 in the lateral direction is desired. As a further example, the length of each of the connecting legs of the horseshoe construction of the plate 20 extending to the lateral arms 52 can be shorter or longer as dictated by patient morphology.

Various other modifications and alternative embodiments of the invention in addition to those described herein will be apparent to persons of ordinary skill in the art who have the benefit of the description of the invention. Accordingly, the description, including the appended drawings, is to be construed as illustrative only, with the understanding that preferred embodiments are shown.

The invention claimed is:

1. A system for mechanically fixating a region of a skull to a portion of a spine, the system comprising:
   a plate configured to contact the region of the skull and be secured thereto;
   a spinal rod configured to extend from a first location adjacent to the plate for connection thereto to a second location adjacent at least one vertebra for connection thereto, the rod and the plate forming an angle Φ with respect to one another about a transverse axis relative to the spine; and
   a variable connection configured to secure the rod to the plate, the variable connection having:
      a first mode connecting the rod and the plate and allowing continuous movement of the rod relative to the plate in a range defined by the angle Φ, wherein the angle Φ can be freely varied relative to the plate without requiring deformation of the rod and the plate; and
      a second mode connecting the rod and the plate wherein the rod and the plate are locked at a particular value of the angle Φ selected to maintain a desired curvature of the spine, wherein the variable connection comprises:
         a lateral arm integral with the plate and extending laterally along the transverse axis relative to the spine; and
         a connector comprising a body having a transverse opening configured to receive the arm and a longitudinal opening configured to receive a proximate portion of the rod adjacent the plate, the transverse opening configured to pivot about the transverse axis in the first mode, wherein the body has a lock opening connecting the transverse and longitudinal openings and extending normal to the transverse and longitudinal openings, and wherein the connector further comprises:
            a clamp plug configured to be received in the lock opening at a location between the transverse and longitudinal openings; and
            a lock configured to engage the lock opening and the lateral arm, wherein the clamp plug and the lock are configured to operate in the lock opening to allow free rotational and translation movement of the lateral arm and the rod in the transverse and longitudinal openings in the first mode and to clamp the lateral arm, the clamp plug, and the rod against the rotational and translation movements in the second mode.

2. The system of claim 1 wherein the connection is configured to also allow the rod to be adjusted laterally with respect to the plate in the first mode without requiring deformation of the rod and the plate, and to be locked at a lateral position relative to the plate in the second mode.

3. The system of claim 1 wherein the connection is configured to also allow the rod to be adjusted longitudinally with respect to the plate in the first mode without requiring deformation of the rod and the plate, and to be locked at a longitudinal position relative to the plate in the second mode.

4. The system of claim 1 wherein the connection is configured to allow a second angle formed between the rod and the plate to be adjusted in the first mode without requiring deformation of the rod and the plate, and for the rod and the plate to be locked at a particular value of the angle in the second angle in the second mode.

5. The system of claim 1 wherein the lateral arm and the transverse opening are configured to also allow the connector to be adjusted laterally with respect to the plate in the first mode without requiring deformation of the rod and the plate, and to be locked at a lateral position relative to the plate in the second mode.

6. The system of claim 1 wherein the longitudinal opening is configured to also allow the rod to be adjusted longitudinally with respect to the plate in the first mode without requiring deformation of the rod and the plate, and to be locked at a longitudinal position relative to the plate in the second mode.

7. The system of claim 1 wherein the lateral arm and the transverse opening are configured to allow a second angle formed between the rod and the plate to be adjusted in the first mode without requiring deformation of the rod and the plate, and for the rod and the plate to be locked at a particular value of the second angle in the second mode.

8. The system of claim 1 wherein the lateral arm has a first set of spline teeth and the plug has a second set of spline teeth, the first and second sets of spline teeth being disengaged in the first mode and engaged in the second mode.

9. The system of claim 1 wherein the lock has external threads and the locking opening has internal threads that mate with the external threads in both the first and second modes.

10. The system of claim 1 further comprising:
a second spinal rod configured to extend from a location adjacent to the plate for connection thereto to a location adjacent at least one vertebra for connection thereto, the first and second rods positioned on laterally opposite sides of the plate from each other; and
a second variable connection configured to secure the second rod to the plate, the second connection having a first mode connecting the second rod and the plate wherein an angle formed between the second rod and the plate can be freely varied without requiring deformation of the second rod and the plate and a second mode connecting the second rod and the plate wherein the second rod and the plate are locked at a particular value of the angle selected to maintain a desired curvature of the spine.

11. A system for mechanically fixating a region of a skull to a portion of a spine, the system comprising:
a plate configured to contact the region of the skull and be secured thereto;
a spinal rod configured to extend from a first location adjacent to the plate for connection thereto to a second location adjacent at least one vertebra for connection thereto;
a variable connection configured to secure the rod to the plate, the variable connection having first and second modes connecting the rod and the plate:
in the first mode the rod being freely rotatable relative to the plate in a range defined by an angle $\Phi$ formed by the rod relative to the plate, a relative position of the rod and the plate being adjustable with respect to at least four degrees of freedom of motion without requiring deformation of the rod and the plate; and
in the second mode the rod and the plate being locked in a particular relative position with respect to the at least four degrees of freedom of motion to maintain a desired curvature of the spine, wherein the variable connection comprises:
a lateral arm integral with the plate and extending laterally along the transverse axis relative to the spine; and
a connector comprising a body having a transverse opening configured to receive the arm and a longitudinal opening configured to receive a proximate portion of the rod adjacent the plate, the transverse opening configured to pivot about the transverse axis in the first mode, wherein the body has a lock opening connecting the transverse and longitudinal openings and extending normal to the transverse and longitudinal openings, and wherein the connector further comprises:
a clamp plug configured to be received in the lock opening at a location between the transverse and longitudinal openings; and
a lock configured to engage the lock opening and the lateral arm, wherein the clamp plug and the lock are configured to operate in the lock opening to allow free rotational and translation movement of the lateral arm and the rod in the transverse and longitudinal openings in the first mode and to clamp the lateral arm, the clamp plug, and the rod against the rotational and translation movements in the second mode.

12. The system of claim 11 wherein the variable connection is configured to allow adjustment of the relative position for the rod and the plate with respect to a fifth degree of freedom of motion in the first mode without requiring deformation of the rod and the plate.

13. The system of claim 11 wherein one of the degrees of freedom of motion is a rotation or pivoting of the variable connection about a laterally extending axis relative to the spine.

14. The system of claim 11 wherein one of the degrees of freedom of motion is a rotation of the variable connection about an axis that is perpendicular to a laterally extending axis and a longitudinally extending axis relative to the spine.

15. The system of claim 11 wherein one of the degrees of freedom of motion is a translation of the variable connection along a laterally extending axis relative to the spine.

16. The system of claim 11 wherein one of the degrees of freedom of motion is a translation of the rod along a longitudinally extending axis relative to the spine.

17. The system of claim 11 wherein one of the degrees of freedom of motion is a rotation of the rod about a longitudinally extending axis relative to the spine.

18. The system of claim 13 wherein the at least four degrees of freedom of motion comprises:
a rotation of the variable connection about an axis that is perpendicular to the laterally extending axis and a longitudinally extending axis relative to the spine;
a translation of the variable connection along the laterally extending axis;
a translation of the rod along the longitudinally extending axis; and
a rotation of the rod about the longitudinally extending axis.

19. The system of claim 11 further comprising:
a second spinal rod configured to extend from a location adjacent to the plate for connection thereto to a location adjacent at least one vertebra for connection thereto, the first and second rods positioned on laterally opposite sides of the plate from each other;

a second variable connection configured to secure the second rod to the plate, the second connection having first and second modes connecting the second rod and the plate, in the first mode a relative position of the second rod and the plate being adjustable with respect to at least four degrees of freedom of motion without requiring deformation of the second rod and the plate, in the second mode the second rod and the plate being locked in a particular relative position with respect to the at least four degrees of freedom of motion to maintain a desired curvature of the spine.

20. A method of coupling a plate to a rod in a system where the plate is to be secured to a region of a skull and the rod is to be secured to at least one vertebra of a spine, the method comprising the steps of:
   connecting the rod and a portion of the plate via a variable connection to form a relative angle $\Phi$ between the rod and a plane defined by the plate;
   in a first mode of the variable connection, freely rotating the rod relative to the plate in a range defined by the angle $\Phi$, thereby adjusting the relative angle $\Phi$ about a transverse axis relative to the spine to a particular value of the angle $\Phi$ selected to position the skull relative to the spine and define a desired curvature of the spine without requiring deformation of the rod or the plate; and
   in a second mode of the variable connection, locking the rod and the plate to maintain the particular value of the angle $\Phi$ between the rod and the plane defined by the plate, wherein the variable connection comprises:
      a lateral arm integral with the plate and extending laterally along the transverse axis relative to the spine; and
      a connector comprising a body having a transverse opening configured to receive the arm and a longitudinal opening configured to receive a proximate portion of the rod adjacent the plate, the transverse opening configured to pivot about the transverse axis in the first mode, wherein the body has a lock opening connecting the transverse and longitudinal openings and extending normal to the transverse and longitudinal openings, and wherein the connector further comprises:
         a clamp plug configured to be received in the lock opening at a location between the transverse and longitudinal openings; and
         a lock configured to engage the lock opening and the lateral arm, wherein the clamp plug and the lock are configured to operate in the lock opening to allow free rotational and translation movement of the lateral arm and the rod in the transverse and longitudinal openings in the first mode and to clamp the lateral arm, the clamp plug, and the rod against the rotational and translation movements in the second mode.

21. The method of claim 20 further comprising the step of:
adjusting a lateral position of the rod relative to the plate without requiring deformation of the rod or the plate.

22. The method of claim 20 further comprising the step of:
adjusting a longitudinal position of the rod relative to the plate without requiring deformation of the rod or the plate.

23. The method of claim 20 further comprising the step of:
adjusting an angular position of the rod relative to the plate about an axis that is perpendicular to both a laterally extending axis and a longitudinally extending axis without requiring deformation of the rod or the plate.

24. The method of claim 20 further comprising the step of:
adjusting an angular position of the rod relative to the plate about a longitudinal axis defined by the rod without requiring deformation of the rod or the plate.

25. The method of claim 20 further comprising at least three of the following steps:
   adjusting a lateral position of the rod relative to the plate without requiring deformation of the rod or the plate;
   adjusting a longitudinal position of the rod relative to the plate without requiring deformation of the rod or the plate;
   adjusting an angular position of the rod relative to the plate about an axis that is perpendicular to both a laterally extending axis and a longitudinally extending axis without requiring deformation of the rod or the plate; and
   adjusting an angular position of the rod relative to the plate about a longitudinal axis defined by the rod without requiring deformation of the rod or the plate.

26. A method of coupling a plate to a rod in a system where the plate is to be secured to a region of a skull and the rod is to be secured to at least one vertebra of a spine, the method comprising the steps of:
   connecting the rod and a portion of the plate via a variable connection to form a relative position between the rod and a plane defined by the plate;
   in a first mode of the variable connection, adjusting the relative position of the rod and the plate with respect to at least four degrees of freedom of motion comprising:
      a rotation of the variable connection about a laterally extending axis relative to the spine;
      a rotation of the variable connection about an axis that is perpendicular to the laterally extending axis and a longitudinally extending axis relative to the spine;
      a translation of the variable connection along the laterally extending axis; and
      a translation of the rod along the longitudinally extending axis; and
   in a second mode of the variable connection, locking the rod and the plate via the variable connection at a particular relative position with respect to the at least four degrees of freedom of motion to maintain a desired curvature of the spine, wherein the variable connection comprises:
      a lateral arm integral with the plate and extending laterally along the transverse axis relative to the spine; and
      a connector comprising a body having a transverse opening configured to receive the arm and a longitudinal opening configured to receive a proximate portion of the rod adjacent the plate, the transverse opening configured to pivot about the transverse axis in the first mode, wherein the body has a lock opening connecting the transverse and longitudinal openings and extending normal to the transverse and longitudinal openings, and wherein the connector further comprises:
         a clamp plug configured to be received in the lock opening at a location between the transverse and longitudinal openings; and
         a lock configured to engage the lock opening and the lateral arm, wherein the clamp plug and the lock are configured to operate in the lock opening to allow free rotational and translation movement of the lateral arm and the rod in the transverse and longitudinal openings in the first mode and to clamp the lateral arm, the clamp plug, and the rod against the rotational and translation movements in the second mode.

* * * * *